United States Patent [19]

Boghosian et al.

[11] 3,954,965

[45] May 4, 1976

[54] COMPOSITION AND METHOD OF STERILIZING SOFT CONTACT LENSES AND METHOD FOR PREVENTING FORMATION OF PROTEINACEOUS DEPOSITS THEREON

[75] Inventors: Malcolm P. Boghosian, Long Beach; Milagros V. Blanco, Villa Park; Hampar L. Karageozian, Laguna Hills all of Calif.

[73] Assignee: Allergan Pharmaceuticals, Irvine, Calif.

[22] Filed: Dec. 29, 1972

[21] Appl. No.: 319,483

[52] U.S. Cl.................................. 424/81; 424/180; 424/183; 424/280; 424/317; 424/319; 424/322; 424/340; 424/341; 424/343
[51] Int. Cl.² ............... A61K 31/78; A61K 31/045; A61K 31/085; A61L 13/00
[58] Field of Search ........... 424/343, 346, 341, 180, 424/317, 280, 81, 183, 319, 322, 340

[56] References Cited
UNITED STATES PATENTS 3,689,673   9/1972   Phares ................................ 424/326

Primary Examiner—Sam Rosen
Attorney, Agent, or Firm—Martin A. Voet

[57] ABSTRACT

An aqueous, substantially isotonic cleaning and sterilizing solution for plastic hydrophilic soft contact lenses containing as an active ingredient, a compound having the structural formula of

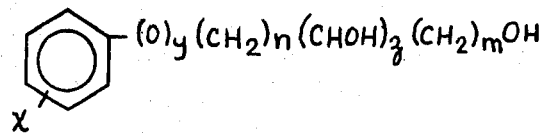

wherein $y$ is 0 or 1, $z$ is 0 or 1, $n$ is from 0–3, $m$ is from 0–3 and $x$ is H or Cl, providing that $n$ and $m$ are not both 0. The foregoing sterilizing solution is non-toxic to the eye of the wearer of the soft contact lens. In the presence of an effective amount of a protein reacting compound, the build-up of proteinaceous deposits on the surface of the soft contact lens is also prevented or inhibited.

8 Claims, No Drawings

COMPOSITION AND METHOD OF STERILIZING SOFT CONTACT LENSES AND METHOD FOR PREVENTING FORMATION OF PROTEINACEOUS DEPOSITS THEREON

BACKGROUND OF THE INVENTION

Hydrophilic or partially hydrophilic plastic materials have been described for use in making so called soft contact lenses. For example, U.S. Pat. No. 3,503,393 to Seiderman and U.S. Pat. No. 2,976,576 to Wichterle describes processes for producing three dimensional hydrophilic polymers of polyhydroxyethylmethacrylate in aqueous reaction media having a sparingly cross-linked polymeric hydrogel structure and having the appearance of elastic, soft, transparent hydrogels. Other soft contact lenses include lenses made out of silicone and other optically suitable flexible materials.

The main virtues of these lenses is their softness and optical suitability. The hydrophilic lenses are particularly useful in ophthalmology due to their remarkable ability to absorb water with a concomitant swelling to a soft mass of extremely good mechanical strength, complete transparency and the ability to retain shape and dimensions when equilibrated in a given fluid.

One of the problems connected with these soft contact lenses is the method of their sterilization and cleaning. The very property of the hydrophilic soft lenses which allows them to absorb up to 150 percent by weight of water also allows preservatives which might otherwise be used for cleaning and sterilization to be absorbed and even concentrated and later released when the soft contact lens is on the eye. The release may be much slower than the uptake; therefore the preservative continues to build-up in the lenses. This build-up eventually effects the physical characteristics of the lenses including dimension, color, etc. This can have the harmful result of damaging or staining the contact lens itself and/or harming the sensitive tissues of the conjunctivae or cornea.

Hard contact lenses do not absorb appreciable amounts of water (i.e. 0.1–0.4%) and thus the use of effective preservatives does not create a problem in the hard contact lens field. However, as stated in U.S. Pat. No. 3,689,673, sterilization of hydrophilic soft contact lenses may be carried out by first soaking in hydrogen peroxide, then sodium bicarbonate and finally normal saline, all at room temperature or by boiling the lenses in normal saline. Furthermore, users of soft contact lenses are warned that under no circumstances should solutions designed for hard contact lenses be used, for the reason that the preservative in such solutions will be absorbed and even concentrated by the soft lens and may seriously damage the soft lens and/or the eye of the user.

Phenylethyl alcohol is known as an effective antibacterial agent in ophthalmic solutions. phenylethyl alcohol is also known to enhance the effect of other bactericides, such as chlorbutanol, benzalkonium chloride, chlorocresol, phenylmercuric nitrate and thimerosal against *P. aeruginosa* in ophthalmic solutions. (J. Amer. Pharm. Assoc. 42: 6–8, 1953; J. Pharm. Pharmac. 171, 23, Suppl. 1415–1465; J. Pharm. Pharmac, 1972, 24, 145–148). Phenylethyl alcohol has the following structural formula:

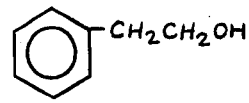

Phenylethyl alcohol

Other related compounds such as 2-phenoxyethanol (phenoxetol) having the structural formula:

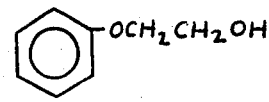

2-phenoxyethanol is also known as a bactericide in conjunction with quarternary ammonium compounds. (The Merck Index, 8th Ed. p. 813).

U.S. Pat. No. 3,689,673 discloses a process of soaking and sterilizing hydrophilic soft contact lenses with chlorhexidene. Therein it is disclosed that a number of commonly used antimicrobial agents including phenethyl alcohol and benyl alcohol are concentrated in the soft lens. The patent also infers that these materials may cause actual corneal damage in rabbits and that similar in vitro and in vivo tests have shown the undesirability of such antimicrobial agents when used with hydrophilic lenses.

It was disclosed in co-pending U.S. application Ser. No. 250,931, filed May 8, 1972, that during toxicity studies on rabbit eyes using plastic hydrophilic soft contact lenses, it was observed that lenses became partially or completely opaque over a period of time. That is, lenses soaked in isotonic saline control and lenses soaked in the test solutions were developing white deposits on the surface of the lenses. The deposits began as tiny white spots along the periphery of the lens finally developing into a complete coating of the lens, thereby making the lens completely opaque. The deposits were strongly attached to the surface of the lens; they could not be removed by gentle rubbing with the tips of the fingers under tap water, or by boiling in isotonic saline solution. Results obtained from clinical studies conducted with volunteer human contact lens wearers indicated that as the deposits built upon the surface of the lens, the patient experienced a great deal of discomfort, as well as blurring of the vision. It was further disclosed in Ser. No. 250,931 that the use of a minor amount of water soluble polyhydroxyethylmethacrylate prevented the formation of these deposits when used in combination with the preserving solution disclosed therein.

SUMMARY OF THE INVENTION

It has now been unexpectedly discovered that soft contact lenses may be effectively sterilized and used without damage to the lenses or injury to the eyes of the user by the method of the present invention which comprises contacting the lens with a sterile, aqueous, substantially isotonic solution containing as an active ingredient, an effective amount of a compound having the structural formula:

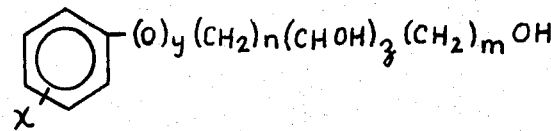

wherein $y$ is 0 or 1, $z$ is 0 or 1, $n$ is from 0–3, $m$ is from 0–3, $x$ is H or Cl and $n$ and $m$ are not both 0, for a time sufficient to substantially sterilize the lens.

The present invention also relates to a sterile, aqueous, substantially isotonic cleaning and sterilizing solution for soft contact lenses comprising the above described solution in combination with an effective amount of a non-toxic protein reacting compound. Proteinaceous materials which would otherwise bind with the surface of the soft contact lens become preferentially bound to the protein reacting compound instead because of the latter's greater reactivity.

The present invention further relates to a method of maintaining soft contact lenses substantially free from surface proteinaceous deposits comprising contacting the soft contact lens with a non-toxic, aqueous solution containing an effective amount of a protein reacting compound.

DESCRIPTION OF THE INVENTION

Notwithstanding the disclosure of U.S. Pat. No. 3,689,673, we have discovered that the aforementioned active ingredient used in the composition and method disclosed herein is safe and effective as a sterilizing agent for hydrophilic soft contact lenses. We have discovered that although the aforementioned active ingredient is initially absorbed in the lens, said active ingredient is entirely and rapidly eluted from the lens when placed in the eye of the wearer. Thus there is no binding or concentrating of the active ingredient in the soft lens. Furthermore, we have discovered that the physical integrity of lenses soaked in solutions containing said active ingredient remains substantially unchanged. The foregoing discoveries are documented in the Examples below.

The active ingredient used in the composition and method disclosed herein is a compound having the structural formula:

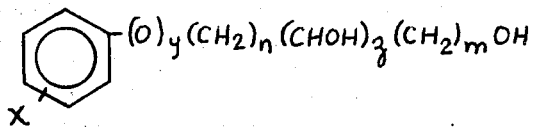

wherein $y$ is 0 or 1, $z$ is 0 or 1, $n$ is from 0–3, $m$ is from 0–3 and $x$ is H or Cl providing that $n$ and $m$ are not both 0. Examples of compounds which may be used in the present invention include phenylethyl alcohol, benzyl alcohol, 2-phenoxyethanol and the non-toxic chloro-substituted analogues thereof, e.g. chlorphenesin.

The amount of the foregoing active ingredient which may be used in the present invention ranges fron about 0.1 to about 1, and preferably about 0.1 to about 0.5% (v/v).

We have now also discovered that the opaque deposits described in Ser. No. 250,931 are basic proteins which carry a positive charge at the pH of tears. It is hypothesized that the charged nature of the protein facilitates interaction with the lens material. The protein also may become associated with the lens by other means, e.g. complex formation, covalent bonding, hydrogen bonds, etc. Opaque deposits are then formed when the protein denatures thereby binding to the lens.

The protein which becomes associated with the lens is denatured (coagulated) by heat, oxidizing agents, heavy metals, etc. We have found that denatured protein attaches more firmly to the lens surface and gradually thickens and inpairs visual acuity of the lens. We have also found that the basic protein which forms deposits on soft contact lenses worn in the human eye is lysozyme or a protein similar in nature to lysozyme as shown in the Examples below.

Lysozyme is an enzyme having an isoelectric point (pI) of 11. That is, at pH 11, a molecule of lysozyme is neutrally charged. At pH below 11, lysozyme is positively charged and at a pH above 11, lysozyme is negatively charged. At the pH of human tears, i.e. pH 6.5–7.5, lysozyme is strongly positively charged. The basic nature of lysozyme is due to the number of basic amino acids in its structure, the most basic of which is arginine.

The protein reacting compounds which may be used in the present invention include water soluble polyhydroxyethylmethacrylate, sodium carboxymethylcellulose, pectin, heparin, propylene glycol alginate, alginic acid chondroitin sulfate, Lytron 810 (Monsanto), polygalacturonic acid, N-acetylglucosamine, di-N-acetylglycosamine, tri-N-acetylglucosamine, chitobiose, chitotriose, chitotetrose, methyl $\beta$-chitobioside, methyl-2-acetamido-2-deoxy-$\beta$-D-glucopyranoside, urea, disodium edetate, succinic acid, malic acid and ascorbic acid.

The water soluble polyhydroxyethylmethacrylate described herein is soluble in alkaline water, the solubility varying with the alkalinity of the water and also on the degree of polymerization. The preferred grade is the polymer with an average molecular weight of about 60,000 to 700,000 and preferably having an average molecular weight of about 80,000 to 225,000. These polymers are available from Hydron Laboratories, e.g. uner the trademark "Hydron Biomedical Polymer, Type Al."

Carboxymethylcellulose or sodium carboxymethylcellulose is a synthetic cellulose gum containing 0.4 to 1.5 sodium carboxymethyl groups ($-CH_2COONa$) per glucose unit of the cellulose. It is a white, odorless, non-toxic hygroscopic powder readily dispersible in hot or cold water. The pH of a 1% solution is 6.5–8.0.

The amount of the protein reacting compounds may be used in the present invention varies from about 0.001 to about 2.0 and preferably from about 0.01 to about 0.1% by weight of the aqueous solution.

The protein reacting compounds described herein have been found to substantially prevent the accumulation of deposits on the surface of the soft contact lenses. The manner in which these polymers prevent the formation of the deposits on the surface of the soft contact lenses is not known. However, it has been hypothesized that positively charged proteinaceous materials which would otherwise react with the soft contact lens react instead with the protein reacting compounds and thereby prevent the deposits from forming on the lenses.

A typical composition of the present invention may contain, in addition to the active ingredients described earlier, buffers, stabilizers and isotonic agents which aid in making the ophthalmic cleaning composition more confortable to the user. These additonal materials must be non-toxic and must not distort the soft lens.

Suitable buffers or stabilizers include sodium or potassium citrate, citric acid, boric acid, various mixed phosphate buffers including combinations of $Na_2HPO_4$, $NaH_2PO_4$, $KH_2PO_4$ and $NaHCO_3$. Generally, buffers and stabilizers may be used in amounts ranging fron about 0.05 to 12.5 and preferably 0.1 to 1.5% (w/v).

The treating solution for contact lenses must be maintained at an osmotic pressure similar to that of physiologic saline, i.e. substantially isotonic, or approximately 0.9% saline, or with suitable agents alone or in combination to render the solution substantially isotonic. Hypotonic solution, e.g. tap e.g., will cause the lens to adhere tightly to the cornea while hypertonic solutions (excess saline) will result in stinging, lacrimation and a red eye.

The above described components of the present invention are non-toxic and are capable of being sterilized without change in composition. Additionally, these components are safe for ophthalmic use with conventional hard contact lenses as well as the "soft" contact lenses.

It should be understood that the foregoing description of the amounts of the various compounds which may be used in the present invention are stated in percentage of ingredients in solution. The formulation may also take the form of one or more conventional solid dosage forms such as tablets suitable for use in a measured quantity of a suitable solvent such as water. The percentage composition of the solid dosage forms is such that when dissolved in a specified volume of water, the solution will have the percentage composition within the ranges set forth in the specification. If solid dosage forms are used, the formulation may include conventional lubricants, binders, and excipients which include gylcerol, sorbitol, boric acid, propylene glycol, polyethylene glycols, dextran and methylcellulose. These materials are used in amounts varying between 0.01 and 10 and preferably between about 0.1 and 5 weight percent.

The method of use of the sterilizing and cleaning solution is the following. The wearer of the soft contact lenses removes them from his eyes and places them in a suitable container with sufficient amount of the composition of the present invention to cover the lenses. The lenses are allowed to soak for at least about 30 minutes and preferable 2 to 8 hours to achieve 99.9% kill of spores, fungi and yeasts. This soaking has been shown to effectively clean and sterilize the lenses and prevent the formation of proteinaceous deposits on the lenses. The foregoing method is carried out at ambient temperature or elevated temperatures, i.e., about 40°-100°C. For example, a contact time of ½ hour at 100°C. has been found satisfactory.

The word "sterilize" is used in the present invention to means the rendering non-viable of substantially all pathogenic bacteria of the type typically found including Gram negative and Gram positive bacterial as well as fungi, except as indicated.

Effective amounts of non-toxic agents suitable for use in substantially sterilizing or preserving soft contact lenses may also be used in combination with the present invention. Examples of non-toxic agents include suitable amounts of water soluble e.g. Na and K, salts of compounds, such as, for example, thimerosal, disodium edetate and mixtures thereof. The foregoing preserving agents may be used in amounts which are non-toxic and which are effective at concentrations varying from about 0.001 to about 1% (w/v).

The above described components of the present invention are non-toxic and are capable of being sterilized without change in composition. additionally, these components are safe for ophthalmic use with conventional hard contact lenses as well as the soft contact lenses.

To illustrate the manner in which the invention may be carried out, the following examples are given. It is understood, however, that the examples are for the purposes of illustration and the invention is not to be regarded as limited to any of the specific materials or conditions set forth therein. Unless otherwise stated "%" means %(w/v).

The rating system devised for specifying the nature of any deposits found on the soft lenses was as follows: If no deposits were visible to the naked eye, the lens was considered to be acceptable. Some "acceptable" lenses had deposits which could be seen under a microscope, but these deposits were not considered significant. If deposits were somewhat visible to the naked eye, and clearly discernible by microscope, the lens was considered to be Type III and potentially harmful. If deposits were clearly visible to the naked eye, the lens was considered Type IV. Type IV lenses were considered to be harmful. In addition, if up to but less than ¼ of the lens surface had deposits, the lens was described as "A". Similarly, the lens was described as a "B" if up to but less than ½ of the lens surface had deposits, "C" if up to, but less than ¾ of the lens surface had deposits and "D" if more than ¾ of the lens surface had deposits.

EXAMPLE I

To test the hypothesis that lysozyme or a lysozyme-like protein was causing the opaque deposits on the soft contact lenses, a laboratory model was developed. A protein solution having a pH of 7.4 was used, as follows:

Protein Solution
0.1% hen-white lysozyme
0.23% $NaH_2PO_4H_2O$
1.15% $Na_2HPO_4$
0.28% NaCL
to 100.00% $H_2O$ Six clean polyhydroxyethylmethacrylate (Bausch & Lomb "Soflens") soft contact lenses were boiled in the protein solution for ½ hour. The lenses were then removed and inspected. All six lenses were found to be coated with a thick Type IV deposit.

EXAMPLE II

Six clean polyhydroxyethylmethacrylate (Bausch & Lomb "Soflens") soft contact lenses were boiled in 0.9% saline for ½ hour. The lenses were then removed and allowed to soak in the Protein Solution of EXAMPLE I. The cycle was repeated as indicated and the lenses were inspected for deposits.

The results of EXAMPLE II are tabulated below in Table 1.

Table 1

| | | No. of lenses which were: | | | | | | | |
| | | III | | | | IV | | | |
| Cycles | Acceptable | A | B | C | D | A | B | C | D |
|---|---|---|---|---|---|---|---|---|---|
| 0 | 6 | — | — | — | — | — | — | — | — |
| 6 | 5 | — | — | 1 | — | — | — | — | — |
| 11 | 4 | — | 1 | 1 | — | — | — | — | — |
| 16 | 4 | — | — | 1 | — | — | — | 1 | — |
| 20 | 4 | — | — | 1 | — | — | — | 1 | — |
| 25 | 4 | — | — | — | — | — | 1 | 1 | — |
| 49 | 2 | 1 | — | 1 | — | — | — | 1 | 1 |

The foregoing EXAMPLE II indicates that the laboratory model deposits protein on the soft lenses within six cycles. Subsequent cycles generally show heavier deposits forming.

EXAMPLE III

EXAMPLE I was repeated except two soft lenses were used and the Protein Solution did not contain phosphate buffer. Both lenses were found to be coated with a thick Type IV deposit.

EXAMPLE IV

Two clean "Soflens" soft contact lenses were soaked for 1 hour in Protein Solutions containing 0.1% lysozyme and citrate-phosphate buffer solutions having pH's of 3.0, 4.0, 5.0, 6.0 and 7.0. The lenses were then soaked overnight in an aqueous solution containing an oxidizing agent which tests had indicated would deposit protein on the lenses. Table 2 below tabulates the results after repeating the foregoing cycle six times (for convenience, "acceptable" is indicated as "I").

Table 2

| Lens | | Cycles | | | | | |
|---|---|---|---|---|---|---|---|
| | | 1 | 2 | 3 | 4 | 5 | 6 |
| pH3 | 1 | I | I | I | I | I | I |
| | 2 | I | I | I | I | III | I |
| pH4 | 1 | I | I | I | III | IV | IV |
| | 2 | I | I | I | I | IV | IV |
| pH5 | 1 | I | I | I | I | IV | IV |
| | 2 | I | I | I | I | IV | IV |
| pH6 | 1 | IV | IV | IV | IV* | IV* | IV* |
| | 2 | III | IV | IV | IV* | IV* | IV* |
| pH7 | 1 | IV | IV | IV | IV | IV | IV |
| | 2 | IV | IV | IV | IV | IV | IV |

*Heavy deposits

The foregoing table shows that the optimum pH for rapid and complete deposition of lysozyme on soft contact lenses is between pH 5-8.

EXAMPLE V

EXAMPLE V describes the procedures used to determine the chemical nature of the white opaque film found on the soft contact lenses. A conventional amino acid analyzer was used. The soft contact lenses used herein were Bausch & Lomb "Soflens" and comprised (1) seven human worn lenses, (2) seven rabbit worn lenses, and (3) four laboratory produced lenses, all of which had heavy opaque deposits on their surfaces. The deposits were produced in humans and rabbits by having the lenses worn by the respective subjects over a period of 2 to 4 weeks for 6-7 hours/day. The lenses were soaked in 0.9% saline overnight between wearings. The opaque deposits on the four laboratory produced lenses were made by the procedure of EXAMPLE I.

Acid Hydrolysis

Four human worn lenses (Sample A), four rabbit worn soft lenses (Sample B), and two laboratory model processed soft lenses (Sample C) were all placed respectively in 10 ml glass ampules. 10 ml of 6N hydrochloric acid was added to each ampule, the contents of each ampule was frozen using an acetone-dry ice bath. The ampules were flushed with nitrogen and sealed. The ampules were placed in an oven at 100°C and maintained at that temperature for 48 hours. After the 48 hours of acid hydrolysis, the hydrochloric acid solutions were evaporated to dryness respectively. The dried samples were redissolved in a total volume of 1.0 ml citrate buffer pH-2.0. The samples were injected into the amino acid analyzer in the conventional manner and the results tabulated.

Basic Hydrolysis

Three human worn soft lenses (Sample D), three rabbit worn soft lenses (Sample E), and two laboratory model processed soft lenses (Sample F) were all placed respectively in 10 ml glass ampules. 10 ml of 6.5% barium hydroxide solution was added to each ampule, the contents of each ampule was frozen using an acetone-dry ice bath. The ampules were flushed with nitrogen and sealed. The ampules were incubated for a period of 48 hours at 100°C. The cooled reaction mixture was adjusted to pH = 6.0 with 2N sulfuric acid, heated to boiling and centrifuged to separate barium sulfate. The supernatant liquid and washings were evaporated to dryness and the residue dissolved in 2 ml of citrate buffer pH-2.0. The samples were injected into the analyzer in the conventional manner, and the results tabulated. Table 3 below tabulates the results of the foregoing analyses on the opaque deposits on the human, rabbit and laboratory-produced lenses and compares the results to published data on human tear lysozyme (*J. Lab and Clin. Med.*, Dec. 1967 pp. 951–962) and hen-white lysozyme (*Biken Journal*, Vol. 9, pp. 107-114, 1966).

Table 3

Ratios of Amino Acids Found in Soft Contact Lens Deposits Compared with Published Ratios of Amino Acids in Human and Hen-White Lysozyme

| Amino Acids | Published Human Tear Lysozyme | Human Lens Deposit | Published Hen-White Lysozyme | Hen-White Lysozyme Lab Model Lens | Rabbit Lens Deposit |
|---|---|---|---|---|---|
| Threonine | 6 | 6 | 7 | 7 | 7 |
| Serine | 7 | 7 | 10 | 10 | 9 |
| Glutamic Acid | 9–10 | 9 | 5 | 5 | 11 |
| Proline | 3 | 5 | 2 | 2 | — |
| Glycine | 11 | 11 | 12 | 12 | 12 |
| Alanine | 12–13 | 10–11 | 12 | 12 | 6 |
| Half Cystine | 6 | — | 8 | — | — |
| Valine | 8 | 6 | 6 | 6 | 6 |
| Methionine | 2 | — | 2 | — | — |
| Isoleucine | 5 | 3–4 | 6 | 6 | 4 |
| Leucine | 8 | 7 | 8 | 8 | 7 |
| Tyrosine | 5 | 4 | 3 | 3 | — |
| Phenylalanine | 2 | 3 | 3 | 3 | 7 |
| Histidine | 1 | 1 | 1 | 1 | 2 |
| Lysine | 5 | 2 | 5 | 5 | 4 |
| Arginine | 11–12 | 10–11 | 11 | 11 | 9 |
| Tryptophane | — | — | — | — | — |

Table 3-continued

Ratios of Amino Acids Found in Soft Contact Lens Deposits
Compared with Published Ratios of Amino Acids in Human
and Hen-White Lysozyme

| Amino Acids | Published Human Tear Lysozyme | Human Lens Deposit | Published Hen-White Lysozyme | Hen-White Lysozyme Lab Model Lens | Rabbit Lens Deposit |
|---|---|---|---|---|---|
| Aspartic Acid | — | — | — | — | — |

Table 3 shows that, as expected, the amino acid ratios of the protein deposited on the soft lenses utilizing the laboratory model compares very closely with the amino acid ratio of published hen-white lysozyme. This would be expected because the laboratory model utilized hen-white lysozyme to coat the lenses.

Table 3 also shows that the amino acid ratio of human soft lens protein compares very closely with the amino acid ratio of published human tear lysozyme inferring very strongly that the protein which is deposited on human worn lenses is lysozyme or a lysozyme-like protein.

The results shown in Table 3 also clearly show the nature of the opaque thin deposits which accumulate on the soft lenses is a protein which is classified as a basic protein due to the high proportions of lysine and arginine present.

It should be noted that the amino acid ratios of human lens protein compared very favorably with laboratory model lens protein, indicating that the laboratory model as a whole is a very good approximation of human soft lens deposition.

Finally, it should be noted that although the protein deposited in the rabbit model is a basic protein, its properties seem to be quite different in its amino acid composition and ratio from either the human lens protein or laboratory model lens protein.

EXAMPLE VI

EXAMPLE II was repeated, except the following protein inhibiting solution was used in place of the saline solution:
Protein Inhibiting Solution
0.1% sodium carboxymethylcellulose
0.85% NaCl
to 100% H$_2$O The results are tabulated in Table 4 below:

Table 4

| | | No. of Lenses which were: | | | | | | | |
|---|---|---|---|---|---|---|---|---|---|
| | | III | | | | IV | | | |
| Cycles | Acceptable | A | B | C | D | A | B | C | D |
| 5 | 6 | — | — | — | — | — | — | — | — |
| 10 | 6 | — | — | — | — | — | — | — | — |
| 16 | 5 | — | — | 1 | — | — | — | — | — |
| 22 | 5 | — | — | 1 | — | — | — | — | — |
| 28 | 5 | — | — | 1 | — | — | — | — | — |
| 33 | 5 | 1 | — | — | — | — | — | — | — |
| 38 | 5 | 1 | — | — | — | — | — | — | — |
| 42 | 5 | 1 | — | — | — | — | — | — | — |
| 47 | 5 | 1 | — | — | — | — | — | — | — |
| 107 | 6 | — | — | — | — | — | — | — | — |
| 148 | 6 | — | — | — | — | — | — | — | — |
| 180 | 4 | — | — | — | 2 | — | — | — | — |

The results indicated that the Protein Inhibiting Solution of EXAMPLE VI reduces substantially the deposits formed on the soft lens compared with the deposits found in EXAMPLE II without use of the Protein Inhibiting Solution.

EXAMPLE VII

EXAMPLE VI was repeated, except the protein inhibiting solution used was as follows:
Protein Inhibiting Solution
0.1% water soluble polyhydroxyethylmethacrylate[1]
0.1% Na$_2$HPO$_4$
0.075% KH$_2$PO$_4$
0.82% NaCl
0.02% polyethylene glycol The results are tabulated in Table 5 below:

Table 5

| | | III | | | | IV | | | |
|---|---|---|---|---|---|---|---|---|---|
| Cycles | Acceptable | A | B | C | D | A | B | C | D |
| 4-21 | 6 | — | — | — | — | — | — | — | — |
| 27 | 5 | 1 | — | — | — | — | — | — | — |
| 32-46 | 6 | — | — | — | — | — | — | — | — |
| 50 | 5 | 1 | — | — | — | — | — | — | — |

[1] Polyhydroxyethylmethacrylate: water soluble, having a mw of 124,500 as determined by Hewlett-Packard Model 502 membrane osmometer.

EXAMPLE VIII a. EXAMPLE VII was repeated, except the water soluble polyhydroxyethylmethacrylate in the Protein Inhibiting Solution was replaced with propylene glycol alginate. The lenses remained "acceptable" after 115 cycles.

b. EXAMPLE VII was repeated, except that the concentration of water soluble polyhydroxyethylmethacrylate was reduced to 0.01% and 0.05%, respectively. In each case, the lenses remained "acceptable" for the duration of the tests, i.e., 46 cycles for 0.01% and 40 cycles for 0.05% polyhydroxyethylmethacrylate.

EXAMPLES VII and VIII clearly show that water soluble polyhydroxyethylmethacrylate and propylene glycol alginate substantially inhibit the formation of deposits on soft contact lenses.

EXAMPLE IX

EXAMPLE VI was repeated, except that the following Protein Inhibiting formulations were tested for four cycles each:

Protein Inhibiting Solutions:

(1) 0.1% Water soluble polyhydroxyethylmethacrylate[1]
    0.01% NaHCO$_3$
    0.1% boric acid
    0.88% NaCl
    0.02% polyethylene glycol
    to 100% H$_2$O (2) 0.1% Water soluble polyhydroxyethylmethacrylate[1]
    0.01% NaHCO$_3$
    0.1% Na$_2$HPO$_4$
    0.05% KH$_2$PO$_4$
    0.0127% Na$_2$ edetate
    0.84% NaCl
    0.02% polyethylene glycol
    to 100% H$_2$O (3) 0.1% Water soluble polyhydroxyethylmethacrylate[1]
    0.01% NaHCl$_3$ -continued Protein Inhibiting Solutions:

```
    0.05% boric acid
    0.88% NaCl
    0.02% polyethylene glycol
    to 100% H₂O
(4) 0.1% Water soluble polyhydroxyethylmethacrylate¹
    0.01% NaHCO₃
    0.1% boric acid
    0.841% NaCl
    0.02% polyethylene glycol
    to 100% H₂O
```

¹Polyhydroxyethylmethacrylate: Footnote 1, EXAMPLE VI.

The results indicated that no deposits were found on any of the lenses tested.

EXAMPLE X

EXAMPLE VI is repeated, except an equivalent amount of each of the following compounds are substituted for sodium carboxymethylcellulose: urea, pectin, heparin, polygalacturonic acid, N-acetylglucosamine, chitobiose, methyl-2-acetamido-2-deoxy-$\beta$-D-glucopyranoside, disodium edetate, alginic acid, chondroitin sulfate, succinic acid, malic acid and ascorbic acid. Comparable results are obtained.

EXAMPLE XI

An adsorption/elution study was made on polyhydroxyethylmethacrylate plastic hydrophilic (soft) contact lenses with the following formulation having a pH of 8.2:

%
0.2 (v/v) phenylethyl alcohol (PEA)
0.001 thimerosal
0.05 water soluble polyhydroxyethylmethacrylate
0.1 NaHCO₃
0.8 NaCl a. Three soft lenses were soaked separately in 10.0 ml of the solution for 8 hours in a glass with a polyethylene cap. As a control, 10 ml of the solution was kept in the same type of container in the absence of a lens. At the end of the soaking period, the amount of PEA remaining in each jar was measured by direct UV method. The difference between the PEA in the control and the PEA in solution with the lens was considered the amount taken up the lens. Subsequently, each lens was rinsed by dipping it in a large volume (1 liter) of water and then transferring it into 10.0 ml of isotonic saline for 16 hours. Then the solution was analyzed for eluted PEA.

The foregoing procedures were carried out at 23°C. and 32°C. and 45°C. over a period of 2 weeks with analysis done only during 5 working days of the week.

It was found that the maximum amount that a lens absorbed from 10 ml was about 0.4 mg or about 1.2% of the lens (based on wet weight of the lens of 33 mg). The results also showed that the amount lost or absorbed by the lens was completely eluted out. That is, the % PEA remaining + %PEA eluted = %PEA initial. Based on the foregoing, it can be stated that PEA does not concentrate in the soft lens. This result was confirmed by direct UV analysis for PEA in the eluted lenses. No PEA was found by this method of analysis. (The analysis techniques used were capable of detecting as little as 0.001% PEA.)

b. EXAMPLE XI(a) was repeated, except the elution period was 30 minutes following a 16 hour soak in the PEA solution. 100% elution of PEA was obtained.

c. EXAMPLE XI(a) was repeated, except the study was in vivo rather than in vitro. The study consisted of placing the lenses in the left eyes of four albino rabbits for 1-½ hours after soaking in the PEA solution. The lenses were then removed and analyzed for the presence of PEA by UV light. No PEA was found in the lenses.

EXAMPLE XII

This EXAMPLE XII was designed to determine the effect of the formulation of EXAMPLE XI on the physical integrity of soft lenses soaked in it. It is known that soft lenses may change shape, size and even color, depending upon the solution in which they are soaked. Soaking at elevated temperature (32°C., 45°C.) gives an accelerated effect over the effect obtained by soaking at ambient temperature.

a. Four soft polyhydroxyeethylmethacrylate lenses were used for each temperature (23°C., 32°C., 45°C.). The soaking jars used were glass bottles (20 cc) with polyethylene caps. Initial diameter, and power of the lenses were measured. The soft lenses were then soaked in the formulation of EXAMPLE XI for 8 hours. The lenses were then rinsed quickly with isotonic saline and then soaked in saline for 16 hours (simulated normal wear time). The soaking procedure was repeated daily for the five working days in a week for four weeks; lenses were kept in saline over weekends.

Table 4 below tabulates the results of the foregoing study:

Table 4

| Lenses | Initial | | After 30 Days* | | |
|---|---|---|---|---|---|
| | Diameter | Power | Diameter | Power | % H₂O |
| At 23°C | 12.3 | −1⅞ | 12.2 | −1¾ | 36.96 |
| | 12.3 | −1¾ | 12.3 | −1¾ | 36.05 |
| | 12.2 | −1⅞ | 12.3 | −1¾ | 35.09 |
| At 32°C | 12.5 | −1¾ | 12.3 | −1¾ | 35.00 |
| | 12.2 | −1⅞ | 12.4 | −1⅝ | 35.92 |
| | 12.2 | −1⅞ | 12.3 | −1¾ | 34.90 |
| At 45°C | 12.3 | −1⅞ | 12.2 | −1⅝ | 35.09 |
| | 12.2 | −1¾ | 12.4 | −1⅝ | 36.02 |
| | 12.6 | −1¾ | 12.3 | −1⅝ | 36.15 |

*Color of lenses did not change

As is apparent from Table 4, the solution did not cause any noticeable and measurable effect on the lenses kept at 23°C., 32°C., and 45°C., after 30 days.

b. EXAMPLE XI(a) was continued for 90 days. Comparable results were obtained.

EXAMPLE XIII

To determine whether the formulation used in EXAMPLE XI was toxic, the following study was undertaken:

a. Three New Zealand albino rabbits received two drops of the formulation of EXAMPLE XI, administered topically into one eye of each of the rabbits every ½ hour for 7 hours. At the end of 7 hours, there was no mucosal irritation in either of the rabbits' eyes.

b. Three New Zealand albino rabbits were fitted in one eye with hydrophilic polyhydroxyethylmethacrylate soft contact lenses which had been soaked over night in the formulation of EXAMPLE XI. The formulation was again administered topically, two drops every ½ hour for 7 hours. Comfort was acceptable and there was no mucosal irritation.

The foregoing study showed that the formulation of EXAMPLE XI was not irritating to rabbit eye mucosae following excessive administration of the formulation in the presence and absence of soft lenses.

EXAMPLE XIV

The left eyes of nine adult female New Zealand albino rabbits were fitted with hydrophilic polyhydroxyethylmethacrylate soft contact lenses. The lenses were soaked overnight in the formulations of EXAMPLE XI and worn by the rabbits for 7 hours daily. After 57 consecutive days of testing, no untoward ocular reactions were observed in any of the test rabbits.

With respect to the formation of opaque deposits on the surface of the lenses after 57 days, seven lenses were clear (no deposits visible to the naked eye) and one had developed opaque deposits after 27 days (one clear lens was lost on the 9th day).

EXAMPLE XV

A number of formulations were tested for antimicrobial activity, each formulation containing 0.1% NaHCO$_3$, 0.8% NaCl, 0.001% thimerosal and 0.05% water soluble polyhydroxyethylmethacrylate, in addition to the ingredients shown:

| Formulation | pH | PEA (% v/v) | Chlorophenoxetol (%) |
|---|---|---|---|
| 1 | 8.0 | 0.05 | 0.05 |
| 2 | 8.05 | 0.05 | — |
| 3 | 8.25 | 0.2 | — |
| 4 | 8.2 | 0.4 | — |
| 5 | 8.3 | — | 0.05 |

The above solutions were challenged by four standard organisms, namely, S, marcescens, S. aureus, C. albicans, and A. niger by the following procedure. 10 ml aleqouts of solution were inoculated to contain approximately 10$^5$ cells/ml. After 6 hours contact time, the remaining number of viable cells was quantitated by 10 fold dilutions in broth media and plated on spread ager plates. Formulations 1 and 2 were found to have inadequate activity against S. aureus, C. albicans, and A. niger. Formulation 3 showed very satisfactory activity (less than 10$^2$ cells/ml) against all organisms. Formulation 4 showed good activity against S. aureus, C. albicans, and S. marcescens, but A. niger was reduced only 2 logs to about 10$^3$ cells/ml. Formulation 5 had good activity only against A. niger.

EXAMPLE XVI

EXAMPLE XV was repeated, except the following formulations were tested, each containing 0.8% NaCl, 0.1% NaHCO$_3$, and 0.05% polyhydroxyethylmethacrylate, and the test organisms were S. aureus, C. albicans, and A. niger.

| Formulation | pH | benzyl alcohol (%) | chlorophenoxitol (%) | Thimerosal (%) |
|---|---|---|---|---|
| 6 | 8.0 | 0.05 | 0.05 | 0.001 |
| 7 | 8.35 | 0.1 | 0.1 | " |
| 8 | 8.5 | 0.5 | — | " |
| 9 | 8.05 | 0.4 | — | " |
| 10 | 8.10 | 0.3 | — | " |
| 11 | 8.10 | 0.3 | — | 0.002 |
| 12 | 8.10 | 0.2 | — | 0.004 |

Table 5 below tabulates the results of the foregoing tests:

Table 5

| | Formulations | | | | | | |
|---|---|---|---|---|---|---|---|
| | 6 | 7 | 8 | 9 | 10 | 11 | 12 |
| S. aureus | 2 × 10$^3$ | <10$^2$ | <10$^2$ | 1 × 10$^4$ | 2 × 10$^4$ | 4 × 10$^4$ | 2 × 10$^3$ |
| C. albicans | <10$^2$ | <10$^2$ | <10 | 1 × 10$^2$ | <10$^2$ | 6 × 10$^2$ | <10$^2$ |
| A. niger | <10$^2$ | <10$^2$ | <10$^2$ | 1 × 10$^2$ | <10$^2$ | <10$^2$ | <10$^2$ |

Of the two formulations containing benzyl alcohol and chlorophenoxetol, the one with the higher concentrations of these two ingredients (formulation 7) was most effective antimicrobial formulation.

We claim:

1. A composition for preventing the formation of proteinaceous deposits on plastic hydrophilic soft contact lenses and for sterilizing the same comprising an aqueous, non-toxic, substantially isotonic solution containing as active ingredients, an effective amount of a sterilizing compound having the formula:

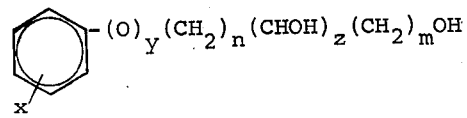

wherein $y$ is 0 or 1, $z$ is 0 or 1, $n$ is from 0–3, $m$ is from 0–3, and $n$ and $m$ are not both 0, and $x$ is selected from the group consisting of H and Cl, and an effective amount of a non-toxic protein reacting compound to substantially prevent the accumulation of deposits on the lens.

2. The composition of claim 1 wherein the sterilizing compond is phenylethyl alcohol.

3. The composition of claim 2 wherein an effective amount of phenylethyl alcohol is about 0.1 to about 1% (v/v).

4. The composition of claim 1 wherein the protein reacting compound is selected from the group consisting of water soluble polyhydroxyethylmethacrylate, carboxymethylcellulose, alginic acid and mixtures thereof.

5. The composition of claim 1 additionally containing an effective amount of thimerosal.

6. A method for sterilizing plastic hydrophilic soft contact lenses and preventing the formation of proteinaceous deposits thereon comprising contacting the lens with the composition of claim 1 for a time sufficient to substantially sterilize the lens and to maintain the lens surface substantially protein free.

7. An aqueous, substantially isotonic solution comprising about 0.2% (v/v) phenylethyl alcohol, about 0.001% (w/v) thimerosal and about 0.05% (w/v) water soluble polyhydroxyethylmethacrylate.

8. A method for sterilizing plastic hydrophilic soft contact lens and preventing the formation of proteinaceous deposits thereon comprising contacting the lens with the composition of claim 7 for a time sufficient to substantially sterilize the lens and to maintain the lens surface substantially protein free.

* * * * *